United States Patent [19]
Fujii et al.

[11] Patent Number: 5,763,218
[45] Date of Patent: Jun. 9, 1998

[54] NUCLEIC ACID ENCODING NOVEL HUMAN G-PROTEIN COUPLED RECEPTOR

[75] Inventors: Ryo Fujii; Shuji Hinuma, both of Tsukuba, Japan; Yi Li, Gaithersburg; Steven M. Ruben, Olney, both of Md.; Daniel R. Soppet, Centreville, Va.

[73] Assignees: Human Genome Science, Inc., Rockville, Md.; Takeda, Osaka, Japan

[21] Appl. No.: 696,770

[22] Filed: Aug. 14, 1996

Related U.S. Application Data

[60] Provisional application No. 60/017,954, May 20, 1996.

[51] Int. Cl.$^6$ .................... C12N 15/12; C07K 14/705
[52] U.S. Cl. ................ 435/69.1; 536/23.5; 435/325; 435/252.3; 435/254.11; 435/320.1
[58] Field of Search .................................. 435/69.1, 325, 435/252.3, 254.11, 320.1; 536/23.5

[56] References Cited

PUBLICATIONS

Murphy, T. C. and Samson, W. K., "The Novel Vasoactive Hormone, Adrenomedullin, Inhibits Water Drinking in the Rat", Endocrinology, 1995, 136:2459–2463.

Ishiyama, Y., et al., "Hemodynamic effects of a novel hypotensive peptide, human adrenomedullin, in rats", Eur. J. Pharmacol., 1993, 241:271–273.

Lippton, H., et al., "Adrenomedullin dilates the pulmonary vascular bed in vivo", J. Appl. Physiol., 1994, 76:2154–2156.

Kanazawa, H., et al., "Adrenomedullin, A Newly Discovered Hypotensive Peptide, is a Potent Bronchodilator", Biochem Biophys Res Commun., 1994, 205:251–254.

Kitamura, K., et al., "Adrenomedullin: A Novel Hypotensive Peptide Isolated From Human Pheochromocytoma", Biochem. Biophys. Res. Comm., 1993, 192:553–560.

Ross, P. C., et al., "RTA, a candidate G protein-coupled receptor: Cloning, sequencing, and tissue distribution", Proc. Natl Acad. Sci. USA, 1990, 87:3052–3056.

Okazaki, H., et al., "Molecular Cloning of a Novel Putative G Protein-Coupled Receptor Expressed in the Cardiovascular System", Chem. Bio. Res. Comm., 1993, 190(3):1104–1109.

Eva, C., et al., "Molecular cloning of a novel G protein-coupled receptor that may belong to the neuropeptide receptor family", Febs, 1990, 271:81–84.

Hla, T., and Maciag, T., "An Abundant Transcript Induced in Differentiating Human Endothelial Cells Encodes a Polypeptide with Structural Similarities to G-protein-coupled Receptors", J. Biol. Chem., 1990, 9308–9313.

Libert, F., et al., "Selective Amplification and Cloning of Four New Members of the G Protein-Coupled Receptor Family", Reports, 1989, 244:569–572.

Kapas et al., J. Biol. Chem., 270, 25344–25347, 1995, Oct. 1995.

*Primary Examiner*—Sally P. Teng
*Attorney, Agent, or Firm*—William T. Han; William T. King; Edward T. Lentz

[57] ABSTRACT

Human G-protein coupled receptor polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the G-protein coupled receptor polypeptides, respectively. Also disclosed are diagnostic methods for detecting a mutation in the G-protein coupled receptor nucleic acid sequences and an altered level of the soluble form of the receptors.

12 Claims, 3 Drawing Sheets

```
 61 CCTACCAGTGACCTTGGAGAGATCCACAACTGGACCGAGCTGCTTGACCTCTTCAACCAC        120
 19 ProThrSerAspLeuGlyGluIleHisAsnTrpThrGluLeuLeuAspLeuPheAsnHis         38

121 ACTTTGTCTGAGTGCCACGTGGAGCTCAGCCAGAGCACCAAGCGCGTGGTCCTCTTTGCC        180
 39 ThrLeuSerGluCysHisValGluLeuSerGlnSerThrLysArgValValLeuPheAla         58

181 CTCTACCTGGCCATGTTTGTGGTTGGGCTGGTGGAGAACCTCCTGGTGATATGCGTCAAC        240
 59 LeuTyrLeuAlaMetPheValValGlyLeuValGluAsnLeuLeuValIleCysValAsn         78

241 TGGCGCGGCTCAGGCCGGGCAGGGCTGATGAACCTCTACATCCTCAACATGGCCATCGCG        300
 79 TrpArgGlySerGlyArgAlaGlyLeuMetAsnLeuTyrIleLeuAsnMetAlaIleAla         98

301 GACCTGGGCATTGTCCTGTCTCTGCCCGTGTGGATGCTGGAGGTCACGCTGGACTACACC        360
 99 AspLeuGlyIleValLeuSerLeuProValTrpMetLeuGluValThrLeuAspTyrThr        118

361 TGGCTCTGGGGCAGCTTCTCCTGCCGCTTCACTCACTACTTCTACTTTGTCAACATGTAT        420
119 TrpLeuTrpGlySerPheSerCysArgPheThrHisTyrPheTyrPheValAsnMetTyr        138

421 AGCAGCATCTTCTTCCTGGTGTGCCTCAGTGTCGACCGCTATGTCACCCTCACCAGCGCC        480
139 SerSerIlePhePheLeuValCysLeuSerValAspArgTyrValThrLeuThrSerAla        158

481 TCCCCCTCCTGGCAGCGTTACCAGCACCGAGTGCGGCGGGCCATGTGTGCAGGCATCTGG        540
159 SerProSerTrpGlnArgTyrGlnHisArgValArgArgAlaMetCysAlaGlyIleTrp        178

541 GTCCTCTCGGCCATCATCCCGCTGCCTGAGGTGGTCCACATCCAGCTGGTGGAGGGCCCT        600
179 ValLeuSerAlaIleIleProLeuProGluValValHisIleGlnLeuValGluGlyPro        198

601 GAGCCCATGTGCCTCTTCATGGCACCTTTTGAAACGTACAGCACCTGGGCCCTGGCGGTG        660
199 GluProMetCysLeuPheMetAlaProPheGluThrTyrSerThrTrpAlaLeuAlaVal        218

661 GCCCTGTCCACCACCATCCTGGGCTTCCTGCTGCCCTTCCCTCTCATCACAGTCTTCAAT        720
219 AlaLeuSerThrThrIleLeuGlyPheLeuLeuProPheProLeuIleThrValPheAsn        238

721 GTGCTGACAGCCTGCCGGCTGCGGCAGCCAGGACAACCCAAGAGCCGGCGCCACTGCCTG        780
239 ValLeuThrAlaCysArgLeuArgGlnProGlyGlnProLysSerArgArgHisCysLeu        258

781 CTGCTGTGCGCCTACGTGGCCGTCTTTGTCATGTGCTGGCTGCCCTATCATGTGACCCTG        840
259 LeuLeuCysAlaTyrValAlaValPheValMetCysTrpLeuProTyrHisValThrLeu        278

841 CTGCTGCTCACACTGCATGGGACCCACATCTCCCTCCACTGCCACCTGGTCCACCTGCTC        900
279 LeuLeuLeuThrLeuHisGlyThrHisIleSerLeuHisCysHisLeuValHisLeuLeu        298

901 TACTTCTTCTATGATGTCATTGACTGCTTCTCCATGCTGCACTGTGTCATCAACCCCATC        960
299 TyrPhePheTyrAspValIleAspCysPheSerMetLeuHisCysValIleAsnProIle        318

961 CTTTACAACTTTCTCAGCCCACACTTCCGGGGCCGGCTCCTGAATGCTGTAGTCCATTAC       1020
319 LeuTyrAsnPheLeuSerProHisPheArgGlyArgLeuLeuAsnAlaValValHisTyr        338
```

FIG. 1A

```
1021 CTTCCTAAGGACCAGACCAAGGCGGGCACATGCGCCTCCTCTTCCTCCTGTTCCACCCAG    1080
 339 LeuProLysAspGlnThrLysAlaGlyThrCysAlaSerSerSerSerCysSerThrGln     358

1081 CATTCCATCATCATCACCAAGGGTGATAGCCAGCCTGCTGCAGCAGCCCCCCACCCTGAG    1140
 359 HisSerIleIleIleThrLysGlyAspSerGlnProAlaAlaAlaAlaProHisProGlu     378

1141 CCAAGCCTGAGCTTTCAGGCACACCATTTGCTTCCAAATACTTCCCCCATCTCTCCCACT    1200
 379 ProSerLeuSerPheGlnAlaHisHisLeuLeuProAsnThrSerProIleSerProThr     398

1201 CAGCCTCTTACACCCAGCTGAGGTAGAGGCCAGAC                             1235
 399 GlnProLeuThrProSer***                                            404
```

FIG. 1B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 1235 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GTCCCAATGT CAGTGAAACC CAGCTGGGGG CCTGGCCCCT CGGAGGGGGT CACCGCAGTG    60
CCTACCAGTG ACCTTGGAGA GATCCACAAC TGGACCGAGC TGCTTGACCT CTTCAACCAC   120
ACTTTGTCTG AGTGCCACGT GGAGCTCAGC CAGAGCACCA AGCGCGTGGT CCTCTTTGCC   180
CTCTACCTGG CCATGTTTGT GGTTGGGCTG GTGGAGAACC TCCTGGTGAT ATGCGTCAAC   240
TGGCGCGGCT CAGGCCGGGC AGGGCTGATG AACCTCTACA TCCTCAACAT GGCCATCGCG   300
GACCTGGGCA TTGTCCTGTC TCTGCCCGTG TGGATGCTGG AGGTCACGCT GGACTACACC   360
TGGCTCTGGG GCAGCTTCTC CTGCCGCTTC ACTCACTACT TCTACTTTGT CAACATGTAT   420
AGCAGCATCT TCTTCCTGGT GTGCCTCAGT GTCGACCGCT ATGTCACCCT CACCAGCGCC   480
TCCCCCTCCT GGCAGCGTTA CCAGCACCGA GTGCGGCGGG CCATGTGTGC AGGCATCTGG   540
GTCCTCTCGG CCATCATCCC GCTGCCTGAG GTGGTCCACA TCCAGCTGGT GGAGGGCCCT   600
GAGCCCATGT GCCTCTTCAT GGCACCTTTT GAAACGTACA GCACCTGGGC CCTGGCGGTG   660
GCCCTGTCCA CCACCATCCT GGGCTTCCTG CTGCCCTTCC CTCTCATCAC AGTCTTCAAT   720
GTGCTGACAG CCTGCCGGCT GCGGCAGCCA GGACAACCCA AGAGCCGGCG CCACTGCCTG   780
CTGCTGTGCG CCTACGTGGC CGTCTTTGTC ATGTGCTGGC TGCCCTATCA TGTGACCCTG   840
CTGCTGCTCA CACTGCATGG GACCCACATC TCCCTCCACT GCCACCTGGT CCACCTGCTC   900
TACTTCTTCT ATGATGTCAT TGACTGCTTC TCCATGCTGC ACTGTGTCAT CAACCCCATC   960
CTTTACAACT TTCTCAGCCC ACACTTCCGG GGCCGGCTCC TGAATGCTGT AGTCCATTAC  1020
CTTCCTAAGG ACCAGACCAA GGCGGGCACA TGCGCCTCCT CTTCCTCCTG TTCCACCCAG  1080
CATTCCATCA TCATCACCAA GGGTGATAGC CAGCCTGCTG CAGCAGCCCC CCACCCTGAG  1140
```

```
CCAAGCCTGA GCTTTCAGGC ACACCATTTG CTTCCAAATA CTTCCCCCAT CTCTCCCACT    1200

CAGCCTCTTA CACCCAGCTG AGGTAGAGGC CAGAC                                1235
```

( 2 ) INFORMATION FOR SEQ ID NO:2:

( i ) SEQUENCE CHARACTERISTICS:
        ( A ) LENGTH: 404 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met Ser Val Lys Pro Ser Trp Gly Pro Gly Pro Ser Glu Gly Val Thr
 1               5                  10                  15

Ala Val Pro Thr Ser Asp Leu Gly Glu Ile His Asn Trp Thr Glu Leu
            20                  25                  30

Leu Asp Leu Phe Asn His Thr Leu Ser Glu Cys His Val Glu Leu Ser
        35                  40                  45

Gln Ser Thr Lys Arg Val Val Leu Phe Ala Leu Tyr Leu Ala Met Phe
    50                  55                  60

Val Val Gly Leu Val Glu Asn Leu Leu Val Ile Cys Val Asn Trp Arg
65                  70                  75                  80

Gly Ser Gly Arg Ala Gly Leu Met Asn Leu Tyr Ile Leu Asn Met Ala
                85                  90                  95

Ile Ala Asp Leu Gly Ile Val Leu Ser Leu Pro Val Trp Met Leu Glu
            100                 105                 110

Val Thr Leu Asp Tyr Thr Trp Leu Trp Gly Ser Phe Ser Cys Arg Phe
        115                 120                 125

Thr His Tyr Phe Tyr Phe Val Asn Met Tyr Ser Ser Ile Phe Phe Leu
    130                 135                 140

Val Cys Leu Ser Val Asp Arg Tyr Val Thr Leu Thr Ser Ala Ser Pro
145                 150                 155                 160

Ser Trp Gln Arg Tyr Gln His Arg Val Arg Arg Ala Met Cys Ala Gly
                165                 170                 175

Ile Trp Val Leu Ser Ala Ile Ile Pro Leu Pro Glu Val Val His Ile
            180                 185                 190

Gln Leu Val Glu Gly Pro Glu Pro Met Cys Leu Phe Met Ala Pro Phe
        195                 200                 205

Glu Thr Tyr Ser Thr Trp Ala Leu Ala Val Ala Leu Ser Thr Thr Ile
    210                 215                 220

Leu Gly Phe Leu Leu Pro Phe Pro Leu Ile Thr Val Phe Asn Val Leu
225                 230                 235                 240

Thr Ala Cys Arg Leu Arg Gln Pro Gly Gln Pro Lys Ser Arg Arg His
                245                 250                 255

Cys Leu Leu Leu Cys Ala Tyr Val Ala Val Phe Val Met Cys Trp Leu
            260                 265                 270

Pro Tyr His Val Thr Leu Leu Leu Leu Thr Leu His Gly Thr His Ile
        275                 280                 285
```

| | | | | | | | | | | | | | | |
|---|---|---|---|---|---|---|---|---|---|---|---|---|---|---|
| Ser | Leu 290 | His | Cys | His | Leu | Val 295 | His | Leu | Leu | Tyr | Phe 300 | Phe | Tyr | Asp | Val |
| Ile 305 | Asp | Cys | Phe | Ser | Met 310 | Leu | His | Cys | Val | Ile 315 | Asn | Pro | Ile | Leu | Tyr 320 |
| Asn | Phe | Leu | Ser | Pro 325 | His | Phe | Arg | Gly | Arg 330 | Leu | Leu | Asn | Ala | Val 335 | Val |
| His | Tyr | Leu | Pro 340 | Lys | Asp | Gln | Thr | Lys 345 | Ala | Gly | Thr | Cys | Ala 350 | Ser | Ser |
| Ser | Ser | Cys 355 | Ser | Thr | Gln | His | Ser 360 | Ile | Ile | Ile | Thr | Lys 365 | Gly | Asp | Ser |
| Gln | Pro 370 | Ala | Ala | Ala | Ala | Pro 375 | His | Pro | Glu | Pro | Ser 380 | Leu | Ser | Phe | Gln |
| Ala 385 | His | His | Leu | Leu | Pro 390 | Asn | Thr | Ser | Pro | Ile 395 | Ser | Pro | Thr | Gln | Pro 400 |
| Leu | Thr | Pro | Ser | | | | | | | | | | | | |

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

TGATAGGGCA GCCAGCACAT GACAAAGACG GC      32

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

AAGGTGCCAT GAAGAGGCAC ATGGGCT      27

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:5:

AGTGACCTTG GAGAGATCCA CAACTGGACC  30

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:6:

ATCCTCAACA TGGCCATCGC GGAACTG  27

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:7:

CGTCGACTGG TCCCAATGTC AGTGAAACC  29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:8:

GTCTGGCCTC TACCTCAGCT GGGTGTAAG                    29

NUCLEIC ACID ENCODING NOVEL HUMAN G-PROTEIN COUPLED RECEPTOR

CROSS-REFERENCE TO RELATED APPLICATION

This application claims priority to provisional application U.S. Ser. No. 60/017,954 filed May 20, 1996, now abandoned.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention are human 7-transmembrane receptors. The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein a-subunits preferentially stimulate particular effectors to modulate various, biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

SUMMARY OF INVENTION

In accordance with one aspect of the present invention, there are provided novel polypeptides as well as biologically active and diagnostically or therapeutically useful fragments and derivatives thereof. The polypeptides of the present invention are of human origin.

In accordance with another aspect of the present invention, there are provided isolated nucleic acid molecules encoding the polypeptide of the present invention including mRNAs, DNAs, cDNAs, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said polypeptide and subsequent recovery of said polypeptide.

In accordance with yet a further aspect of the present invention, there are provided antibodies against such polypeptides.

In accordance with another aspect of the present invention there are provided methods of screening for compounds which bind to and activate or inhibit activation of the receptor polypeptides of the present invention and for receptor ligands.

In accordance with still another embodiment of the present invention there is provided a process of using such activating compounds to stimulate the receptor polypeptide of the present invention for the treatment of conditions related to the under-expression of the G-protein coupled receptors.

In accordance with another aspect of the present invention there is provided a process of using such inhibiting compounds for treating conditions associated with over-expression of the G-protein coupled receptors.

In accordance with yet another aspect of the present invention there is provided non-naturally occurring synthetic, isolated and/or recombinant G-protein coupled receptor polypeptides which are fragments, consensus fragments and/or sequences having conservative amino acid substitutions, of at least one transmembrane domain of the G-protein coupled receptor of the present invention, such that the receptor may bind G-protein coupled receptor ligands, or which may also modulate, quantitatively or qualitatively, G-protein coupled receptor ligand binding.

In accordance with still another aspect of the present invention there are provided synthetic or recombinant G-protein coupled receptor polypeptides, conservative substitution and derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-protein coupled receptors or fragments thereof, as receptor types and subtypes.

In accordance with yet a further aspect of the present invention, there is also provided diagnostic probes comprising nucleic acid molecules of sufficient length to specifically hybridize to the nucleic acid sequences of the present invention.

In accordance with yet another object of the present invention, there is provided a diagnostic assay for detecting a disease or susceptibility to a disease related to a mutation in a nucleic acid sequence of the present invention.

These and other aspects of the present invention should be apparent to those skilled in the art from the teachings herein.

BRIEF DESCRIPTION OF THE DRAWINGS

FIG. 1 shows the cDNA sequence (nucleotide numbers 61-1235 of SEQ ID NO:1) and the corresponding deduced amino acid sequence of the novel G-protein coupled receptor of the present invention, SEQ ID Nos 1 and 2, respectively. Sequencing was performed using a 373 Automated DNA sequencer (Applied Biosystems, Inc.).

DETAILED DESCRIPTION OF THE INVENTION

Figure 2:
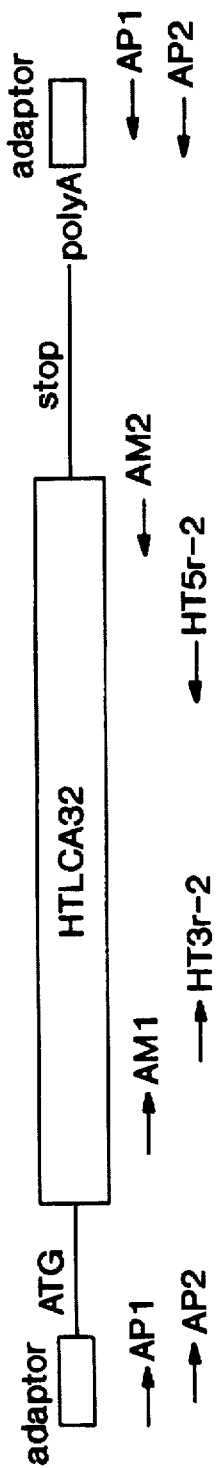
FIG. 2 shows the cloning of 5' and 3' unknown sequence regions of the novel G-protein coupled receptor gene by RACE.

The following drawings are illustrative of embodiments of the invention and are not meant to limit the scope of the invention as encompassed by the claims.

In accordance with an aspect of the present invention, there are provided isolated nucleic acids (polynucleotides) which encode for the mature polypeptide having the deduced amino acid sequence of FIG. 1 (SEQ ID NO:2) or for the mature polypeptide encoded by the cDNA of the clone deposited on Apr. 30, 1996 at the American Type Culture Collection, 12301 Parklawn Drive, Rockville, Md. 20852, U.S.A., as Escherichia coli XL-1 Blue cells containing HTLCA32 plasmid assigned ATCC Deposit No. 98040.

A polynucleotide encoding the polypeptide of the present invention was isolated from a cDNA library derived from human cerebellum tissue. It is structurally related to the G protein-coupled receptor family. It contains an open reading frame encoding a protein of 404 amino acid residues. The protein exhibits the highest degree of homology to a rat adrenomedullin receptor with 74% identity and 94% similarity over a 372 amino acid stretch. Adrenomedullin (AM) is a potent vasodilator peptide that exerts major effects on cardiovascular functions. Its systemic administration causes a rapid and profound fall in blood pressure and an increase in pulmonary blood flow. Its other actions are bronchodilation, being an inhibitor of drinking behavior and an inhibitor of angiotensin-induced aldosterone secretion. All these functions are described in Kapast et al., The Journal of Biological Chemistry, Vol. 270, No. 43, pp 25344–25347, 1995 and in the references cited therein. These above references are incorporated herein by reference in their entirety. Thus, the receptors of the present invention are ultimately useful in treating and diagnosing various diseases and abnormalities connected with these receptors as described hereinbelow.

Potential ligands to the receptor polypeptide of the present invention include but are not limited to adrenomedullin, amylin, CGRP (calcitonin gene ralated proteins), calcitonin, anandamide, serotonin, adrenalin and noradrenalin, platelet activating factor, thrombin, C5a and bradykinin, chemokine, and platelet activating factor.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotides which encode for the mature polypeptides of FIG. 1 (SEQ ID NO:2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variants of the polynucleotides may be a naturally occurring allelic variant of the polynucleotides or a non-naturally occurring variant of the polynucleotides.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotides may have a coding sequence which is a naturally occurring allelic variant of the coding sequence shown in FIG. 1 (SEQ ID NO: 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptides.

The polynucleotides may also encode for a soluble form of the receptor polypeptide of the present invention which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length gene and to isolate other genes which have a high sequence similarity to the gene or similar biological activity. Probes of this type preferably have at least 20 or 30 bases and may contain, for example, 50 or more bases. The probe may also be used to identify a cDNA clone corresponding to a full length transcript and a genomic clone or clones that contain the complete gene of the present invention including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 20 or 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptides of the present invention may be recombinant polypeptides, a natural polypeptides or synthetic polypeptides, preferably recombinant polypeptides.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the G-protein coupled receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHOHS293, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The G-protein coupled receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. coli. In particular, a polynucleotide encoding the receptor of the present invention is employed to transfect cells to thereby express the G-protein coupled receptor. The expressed receptor is then contacted with a test compound to observe binding, stimulation or inhibition of a functional response.

One such screening procedure involves the use of melanophores which are transfected to express the G-protein coupled receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptor on the one hand and which can inhibit the function of a G-protein coupled receptor on the other hand.

For example, compounds which activate the G-protein coupled receptor may be employed for therapeutic purposes, such as the treatment of asthma, Parkinson's disease, acute heart failure, urinary retention, and osteoporosis. In particular, compounds which activate the receptors of the present invention are useful in treating various cardiovascular ailments such as caused by the lack of pulmonary blood flow or hypertension. In addition these compounds may also be used in treating various physiolgical disorders relating to abnormal control of fluid and electrolyte homeostatsis and in diseases associated with abnormal angiotensin-induced aldosterone secretion.

In general, compounds which inhibit activation of the G-protein coupled receptor may be employed for a variety of therapeutic purposes, for example, for the treatment of hypotension and/or hypertension, angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, among others. Compounds which inhibit G-protein coupled receptors have also been useful in reversing endogenous anorexia and in the control of bulimia. In particular, compounds which inhibit the activation of the receptors of the present invention are useful in treating various cardiovascular ailments such as caused by excessive pulmonary blood flow or hypotension. In addition these compounds may also be used in treating various physiolgical disorders relating to abnormal control of fluid and electrolyte homeostatsis and in diseases associated with abnormal angiotensin-induced aldosterone secretion.

An antibody may antagonize a G-protein coupled receptor of the present invention, or in some cases an oligopeptide, which bind to the G-protein coupled receptor but does not elicit a second messenger response such that the activity of the G-protein coupled receptors is prevented. Antibodies include anti-idiotypic antibodies which recognize unique determinants generally associated with the antigen-binding site of an antibody. Potential antagonist compounds also include proteins which are closely related to the ligand of the G-protein coupled receptors, i.e. a fragment of the ligand, which have lost biological function and when binding to the G-protein coupled receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

A small molecule which binds to the G-protein coupled receptor, making it inaccessible to ligands such that normal biological activity is prevented, for example small peptides or peptide-like molecules, may also be used to inhibit activation of the receptor polypeptide of the present invention.

A soluble form of the G-protein coupled receptor, e.g. a fragment of the receptors, may be used to inhibit activation of the receptor by binding to the ligand to a polypeptide of the present invention and preventing the ligand from interacting with membrane bound G-protein coupled receptors.

This invention additionally provides a method of treating an abnormal condition related to an excess of G-protein coupled receptor activity which comprises administering to a subject the inhibitor compounds as hereinabove described along with a pharmaceutically acceptable carrier in an amount effective to inhibit activation by blocking binding of ligands to the G-protein coupled receptors, or by inhibiting a second signal, and thereby alleviating the abnormal conditions.

The invention also provides a method of treating abnormal conditions related to an under-expression of G-protein coupled receptor activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of the G-protein coupled receptor, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions described herein may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein coupled receptor polypeptides, and compounds which activate or inhibit such polypetides are also compounds which may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, y-2, y-AM, PA12, T19-14X, VT-19-17-H2, yCRE, yCRIP, GP+E-86, GP+envAm12, and DAN cell lines as described in Miller, *Human Gene Therapy*, Vol. 1, pg. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor of the present invention can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor.

This invention further provides a method of screening drugs to identify drugs which specifically interact with, and bind to, the human G-protein coupled receptors of the present invention on the surface of a cell which comprises contacting a mammalian cell comprising an isolated DNA molecule encoding the G-protein coupled receptor with a plurality of drugs, determining those drugs which bind to the mammalian cell, and thereby identifying drugs which specifically interact with and bind to a human G-protein coupled receptor of the present invention. Such drugs may then be used therapeutically to either activate or inhibit activation of the receptors of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe of the present invention capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor genes as part of a diagnostic assay for detecting diseases and abnormalities or susceptibility to diseases and abnormalities related to the presence of mutations in the nucleic acid sequences which encode the receptor polypeptides of the present invention. Such diseases, by way of example, are related to cell transformation, such as tumors and cancers and various cardiovascular disorders, including hyper- and hypotention and those arising from abnormal blood flow and abnormal angiotensin-induced aldosterone secretion and other abnormal control of fluid and electrolyte homeostatsis Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor proteins can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Sequence differences between the reference gene and gene having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S 1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptide, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated with disease.

Briefly, sequences can be mapped to chromosomes by preparing PCR primers (preferably 15-25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp.77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 mg of approximately equimolar amounts of the DNA fragments to be ligated.

Unless otherwise stated, transformation is performed as described in the method of Graham, F. and Van der Eb, A., Virology, 52:456-457 (1973). The following examples are for the purpose of illustration only and in no way shall be construed as limiting the scope of the present invention.

EXAMPLE 1
cDNA Synthesis From Human Cerebellum Poly(A)+RNA

Adaptor-ligated double-strand cDNA was prepared by using Marathon cDNA Amplification Kit (Clontech Laboratories, Inc.) from human cerebellum poly(A)+RNA (Nippon Gene Co., Ltd.). The cDNA was diluted to two hundred fold with tricine-EDTA buffer, and this was used as a template DNA for the following PCR.

EXAMPLE 2
Cloning of 5' and 3' Unknown Sequence Regions of the novel G-protein coupled receptor (HTLCA 32) by RACE (Rapid Amplification of cDNA Ends) (FIG. 2)

For cloning 5' and 3' unknown sequence regions of HTLCA32, two primers, namely 5'-TGATAGGGCAGCCAGCACATGACAAAGACGGC-3' (AM2) (SEQ ID NO:3) and 5'-AAGGTGCCATGAAGAGGCACATGGGCT-3' (HT5r-2) (SEQ ID NO:4), were synthesized, on the basis of the sequence of HTLCA32, for 5' region amplification (5'-RACE) and further two primers, namely 5'-AGTGACCTTGGAGAGATCCACAACTGGACC-3' (AM1) (SEQ ID NO:5) and 5'-ATCCTCAACATGGCCATCGCGGAACTG-3 (HT3r-2)

(SEQ ID NO:6) were synthesized (Sequence No. 2) for 3' region amplication (3'-RACE). Using these in combination with the adaptor primers AP I and AP2 attached to Marathon cDNA Amplification Kit, 5'-RACE and 3'-RACE were carried out (FIG. 2). Ex Taq (Takara) was used as DNA polymerase in admixture with an equal amount of Taq Start Antibody (Clontech Laboratories, Inc.) to prevent amplification of nonspecific products and primer dimers. Reaction mixture was prepared by adding 2.5 µl of the buffer attached to Ex Taq. 200 µM dNTPSs, 0.5 µl of the mixed solution of Ex Taq and Taq Start Antibody. 200 nM each primers and 2.5 µl of the template cDNA synthesized in Example 1 were added to the reaction mixture, followed by making the total volume 25 µl with water.

The first PCR reaction was carried out using APi and AM2 for 5'-RACE, and AP1 and AM1 for 3'-RACE. The PCR temperature conditions were as followed: denatured at 94° C. for 1 minute, followed by 5 cycles at 98° C. for 10 seconds and at 72° C. for 5 minutes. 5 cycles at 98° C. for 10 seconds and at 70° C. for 5 minutes, and 25 cycles at 98° C. for 10 seconds and at 68° C. for 5 minutes.

A Gene Amp 9600 termal cycler (Perkin-Elmer) was used. A 1-µl portion of the first PCR reaction mixture was diluted to 100 µl with tricine-EDTA buffer and the second nexted PCR was performed using 2.5 µl of the dilution as a template. AP1 and HT5r-2 were combinedly used as the primers for 5'-RACE while AP2 and HT3r-2 were used as the pimers for 3'-RACE. The reaction mixture was prepared in the same manner as in the first PCR expect for the primer combination and template.

The PCR temperature conditions were was followed: denatured at 94° C. for 1 minute, followed by 5 cycles at 98° C. for 10 seconds and at 72° C. for 5 minutes. 5 cycles at 98° C. for 10 seconds and at 70° C. for 5 minutes, and 22 cycles at 98° C. for 10 seconds and at 68° C. for 5 minutes.

The second PCR products were separated with 1.2% agarose gel and stained with ethidium bromide. Slices of agarose gel containing the band about 700 bp from 5-RACE secondary PCR product and the band about 1200 bp from 3'-RACE secondary PCR product were cut out with a razor blade, and then filtered using an Ultra Free filter unit (Millipore). The eluents were extracted with phenol:chloroform and precipitated in ethanol. Amplification products were subcloned with the TA cloning kit (Invitrogen Co.). The recombinant vectors were introduced into E. Coli JM109 competent cells to produce transformants. Then, transformant clones having a cDNA-inserted fragment were selected in an LB (Luria-Bertani) agar culture medium containing ampicillin, IPTG (isopropylthio-beta-D-galactoside) and X-gal (5-bromo-4-chloro-3-insolyl-beta-D-galactoside). The individual clones were cultured in an LB culture medium containing ampicillin and treated with an automatic plasmid extracting machine (Kurabo) to prepare plasmid DNAs. Sequencing was carried out by using a DyeDeoxy terminator cycle sequencing kit (Perkin-Elmer), the DNA sequences were determined by using a fluorescent automatic sequencer, and the data of the nucleotide sequences obtained were analyzed by using DNASIS (Hitachi System Engineering). As a result, fragments respectively containing the initiation codon and termination codon could successfully be obtained.

EXAMPLE 3
Preparation, by PCR, of cDNA Fragment Containing Full Coding Region of cDNA for the Novel G-Protein Coupled Receptor Based on the sequences obtained in Example 2, the following two primers respectively containing the initiation codon and the termination codon were synthesized:

5'-CGTCGACTGGTCCCAATGTCAGTGAAACC-3'
(HTLCA-F) (Sequence ID No: 7)
5'-GTCTGGCCTCTACCTCAGCTGGGTGTAAG-3'
(HTLCA-R) (Sequence ID No: 8)

HTLCA-F comprises the sequence −6 to 14 (A of the initiation codon ATG being given the number +1) of the DNA defined by Sequence ID No: 1, with a restriction enzyme SalI site being added on the 5' side thereof. HTLCA-R is a sequence complementary to the sequence 1201 to 1229 of the DNA defined by Sequence ID No: 1 and contains the termination codon.

A reaction mixture was prepared in the same manner as in Example 2 except that 2.5 μl of the cDNA prepared in Example 1 was used as a template and HTLCA-F and HTLCA-R were combinedly used as primers. The temperature conditions were denatured at 94° C. for 1 minute, followed by 32 cycles at 98° C. for 10 seconds and at 68° C. for 1 minute. A band (about 1230 bp) thus obtained was recovered in the same manner as in Example 2, for introduction into (*E. coli* JM109) competent cells using a TA cloning kit to give transformants. Sequencing of inserted cDNA fragments revealed that a clone name (*E. coli* JM109/FHTLCA32) had the full coding region of HTLCA32.

What is claimed is:

1. An isolated polynucleotide comprising a polynucleotide selected from the group consisting of:
   (a) a polynucleotide encoding the polypeptide as set forth in SEQ ID NO:2;
   (b) a polynucleotide encoding the polypeptide encoded by the DNA contained in ATCC Deposit No. 98040; and
   (c) a polynucleotide having at least 90% sequence identity to the polynucleotide of (a) or (b).

2. An isolated polynucleotide of claim 1 which comprises a polynucleotide having at least 90% sequence identity to the polynucleotide encoding the polypeptide encoded by the DNA contained in ATCC Deposit No. 98040.

3. An isolated polynucleotide of claim 1 which comprises a polynucleotide having at least 90% sequence identity to a polynucleotide encoding the polypeptide as set forth in SEQ ID NO: 2.

4. An isolated polynucleotide of claim 1 which comprises a polynucleotide having at least 95% sequence identity to a polynucleotide encoding the polypeptide as set forth in SEQ ID NO: 2.

5. An isolated polynucleotide of claim 1 which comprises a polynucleotide encoding the polypeptide of SEQ ID NO:2.

6. A polynucleotide of claim 1 wherein said polynucleotide comprises the sequence as set forth in SEQ ID NO: 1.

7. A vector containing a polynucleotide of claim 1.

8. A host cell transfected or transformed with the vector of claim 7.

9. A process for producing the polypeptide comprising SEQ ID NO: 2 comprising: culturing a host cell of claim 8 under conditions sufficient for the production of said polypeptide and recovering the polypeptide from the culture.

10. A process for producing a polypeptide that binds adrenomedullin, comprising: culturing a host cell of claim 8 under conditions sufficient for the production of said polypeptide and recovering the polypeptide from the culture.

11. A process for producing cells capable of expressing a polypeptide comprising genetically transfecting or transforming cells with the vector of claim 7.

12. A polynucleotide which is a complement of a polynucleotide of claim 1, 2, 3, 4, 5 or 6.

* * * * *